United States Patent
Govari et al.

(10) Patent No.: US 11,867,924 B2
(45) Date of Patent: Jan. 9, 2024

(54) VISUALIZING CATHETER IRRIGATION USING SCHLIEREN IMAGES

(71) Applicant: Biosense Webster (Israel) Ltd., Yokneam (IL)

(72) Inventors: Assaf Govari, Haifa (IL); Amit Fuchs, Hogla (IL); Eran Aharon, Haifa (IL); Yehuda Algawi, Binyamina (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 568 days.

(21) Appl. No.: 17/133,989

(22) Filed: Dec. 24, 2020

(65) Prior Publication Data

US 2022/0202480 A1 Jun. 30, 2022

(51) Int. Cl.
*G02B 27/54* (2006.01)
*G01N 21/45* (2006.01)
*A61B 18/00* (2006.01)

(52) U.S. Cl.
CPC .............. *G02B 27/54* (2013.01); *A61B 18/00* (2013.01); *G01N 21/45* (2013.01); *G01N 21/455* (2013.01)

(58) Field of Classification Search
CPC ......... G02B 27/54; A61B 18/00; A61B 18/14; A61B 2018/00577; A61B 2218/002; A61B 2018/00714; A61B 2018/00982; A61B 18/1492; G01N 21/45; G01N 21/455; A61M 2025/0073; A61M 25/007; A61M 25/00; A61M 2025/0019
USPC ........................................................ 356/129
See application file for complete search history.

(56) References Cited

U.S. PATENT DOCUMENTS

| | | | |
|---|---|---|---|
| 8,052,684 B2 | 11/2011 | Wang et al. | |
| 9,510,853 B2 | 12/2016 | Aljuri et al. | |
| 2003/0133096 A1 | 7/2003 | Aroussi et al. | |
| 2004/0049216 A1 | 3/2004 | Verdaasdonk | |
| 2011/0201929 A1 | 8/2011 | Vaezy et al. | |
| 2012/0101362 A1* | 4/2012 | Weiss ................. | A61B 18/1492 600/411 |
| 2014/0163360 A1* | 6/2014 | Stevens-Wright ... | A61B 5/0036 600/104 |
| 2022/0338921 A1* | 10/2022 | Govari ............... | G01N 15/1463 |

OTHER PUBLICATIONS

Extended European Sear Report dated May 3, 2022, from corresponding European Application No. 21217559.0.

* cited by examiner

*Primary Examiner* — Roy M Punnoose
(74) *Attorney, Agent, or Firm* — Troutman Pepper Hamilton Sanders LLP

(57) ABSTRACT

A system for visualizing catheter irrigation, the system includes a fluid container, a pump, a schlieren imaging assembly and a processor. The fluid container is configured to: (i) contain a first fluid, which is at least partially transparent and has a first temperature, and (ii) receive into the first fluid a catheter having one or more irrigation holes. The pump is configured to inject, through the one or more irrigation holes, a second fluid, which is at least partially transparent and has a second different temperature. The schlieren imaging assembly is configured to acquire schlieren images of turbulence occurring in the first fluid when injecting the second fluid, and the processor is configured to visualize the irrigation using the schlieren images.

16 Claims, 2 Drawing Sheets

VISUALIZING CATHETER IRRIGATION USING SCHLIEREN IMAGES

FIELD OF THE INVENTION

The present invention relates generally to visualizing systems, and particularly to methods and systems for visualizing irrigation of a medical catheter.

BACKGROUND OF THE INVENTION

Schlieren techniques are used for imaging in various applications, such as in some medical imaging.

For example, U.S. Patent Application Publication 2004/0049216 describes a device for perforating tissue, especially for transmyocardial revascularization. The device comprising an ultrasonic generator coupled to an attachable solid needle, and schlieren techniques are used for visualizing the shock waves.

U.S. Patent Application Publication 2011/0201929 describes a plurality of concepts related to HIFU therapy, including a technique to spatially track and display the relative positions of a HIFU focal point and an imaging plane from an ultrasound imager, so that a clinician can ensure that the HIFU focus remains in the image plane during HIFU therapy, thereby facilitating image guided HIFU therapy.

U.S. Patent Application Publication 2003/0133096 describes an optical endoscopic fluid flow measurement probe assembly having a user end and a distal end. The distal end having a light sheet generator and at least one reflected light acquirer, and the endoscope is provided with transmission means to transmit information away from the distal end. The light sheet generator is adapted in use to generate a sheet of light and the light acquirer being adapted to image light reflected from the light sheet, the light sheet generator and light acquirer being provided in the same endoscope.

As shown in FIGS. 1a-1i of the publication "SCHLIEREN IMAGING: A POWERFUL TOOL FOR ATMOSPHERIC PLASMA DIAGNOSTIC" by Enrico Traldi1, Marco Boselli1, Emanuele Simoncelli1, Augusto Stancampiano, Matteo Gherardi1, Vittorio Colombo and Gary S. Settles, published by EPJ Techniques and Instrumentation (2018), which is incorporated by reference herein, eight different arrangements (shown in this publication as FIGS. 1b, 1c, 1d, 1e, 1f, 1g, 1h and 1i) of the Schlieren imaging technique can be utilized from the Schlieren technique first invented by August Toepler in 1859 (shown in FIG. 1a of this publication).

SUMMARY OF THE INVENTION

An embodiment of the present invention that is described herein provides a system for visualizing catheter irrigation, the system includes a fluid container, a pump, a schlieren imaging assembly and a processor. The fluid container is configured to: (i) contain a first fluid, which is at least partially transparent and has a first temperature, and (ii) receive into the first fluid a catheter having one or more irrigation holes. The pump is configured to inject, through the one or more irrigation holes, a second fluid, which is at least partially transparent and has a second different temperature. The schlieren imaging assembly is configured to acquire schlieren images of turbulence occurring in the first fluid when injecting the second fluid. The processor is configured to visualize the irrigation using the schlieren images.

In some embodiments, the first fluid includes water and the second fluid includes water or a saline solution. In other embodiments, the first temperature and the second temperature have a difference of at least 1 degree Celsius. In yet other embodiments, the schlieren imaging assembly includes: (i) one or more illumination sources, such that at least one of the illumination sources is configured to direct a light beam having one or more predefined wavelengths, and (ii) one or more schlieren cameras, configured to acquire the schlieren images.

In an embodiment, the schlieren cameras include: (i) a first schlieren camera, configured to acquire a first schlieren image at a first viewing angle, and (ii) a second schlieren camera, configured to acquire a second schlieren image at a second different viewing angle. In another embodiment, the first and second schlieren images include two-dimensional (2D) schlieren images, and the processor is configured to visualize the irrigation by producing, based on the 2D schlieren images, one or more three-dimensional (3D) schlieren images.

In some embodiments, the processor is configured to display a time-series of the 3D schlieren images in video. In other embodiment, the fluid container is at least partially transparent to the light beam and has a scale, and the processor is configured to calculate a gradient of the temperature, between the first and second temperatures, using the scale.

There is additionally provided, in accordance with an embodiment of the present invention, a method for visualizing catheter irrigation, the method includes, in a fluid container having a first fluid, which is at least partially transparent and has a first temperature, injecting, through one or more irrigation holes of a catheter, a second fluid, which is at least partially transparent and has a second different temperature. Schlieren images of turbulence occurring in the first fluid when injecting the second fluid, are acquired, and the irrigation is visualized using the schlieren images.

The present invention will be more fully understood from the following detailed description of the embodiments thereof, taken together with the drawings in which:

DETAILED DESCRIPTION OF EMBODIMENTS

Overview

Figure 1:
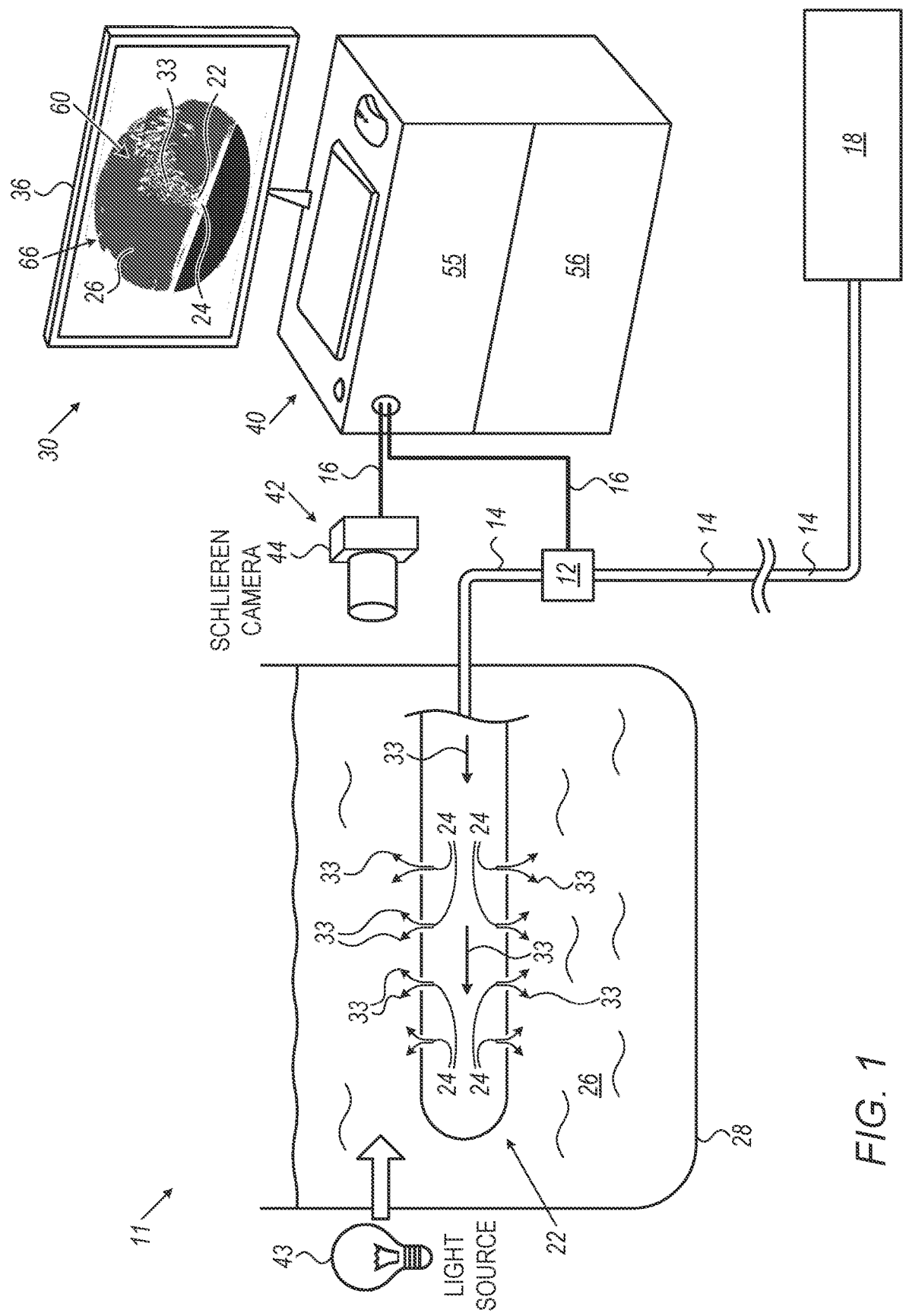
FIG. 1 is a block diagram that schematically illustrates a system for visualizing catheter irrigation, in accordance with an embodiment of the present invention.

In a catheterization procedure, such as radiofrequency (RF) ablation, it is important to estimate the effectiveness of irrigation using an ablation catheter having irrigation holes. In principle, it is possible to estimate the irrigation effectiveness by inserting a catheter into a bath having water, and injecting irrigation fluid with dissolved dye, through irrigation holes of the catheter. However, this method does not allow for continuous estimation of the irrigation effectiveness, because the water bath quickly becomes opaque in the presence of the dissolved dye.

Embodiments of the present invention that are described hereinbelow provide improved techniques for continuously visualizing an irrigation fluid, which is at least partially transparent, and is injected into a testing bath through irrigation holes of the catheter. The visualization may be used for estimating irrigation effectiveness of a catheter, e.g., during a RF ablation procedure.

In some embodiments, a system for visualizing catheter irrigation comprises: (a) a fluid container, (b) a pump, (c) a schlieren imaging assembly, and (d) a processor. Note that the system is typically positioned in a laboratory and serves for improving and/or testing the irrigation effectiveness by visualizing the motion of the irrigation fluid (e.g., a saline solution) injected into fluid (e.g., water) placed within the fluid container.

In some embodiments, the fluid container is transparent to light and configured to contain the water, which is typically transparent and has a temperature resembling the temperature of a patient blood (e.g., between about 36° C. and 38° C.). The fluid container is further configured to receive into the water a catheter having one or more irrigation holes for injecting the irrigation fluid into the container.

In some embodiments, the pump is configured to inject the irrigation fluid, which is at least partially transparent and has a different temperature (e.g., about 50° C., or any other suitable temperature between about 25° C. and 70° C.) through the catheter irrigation holes, into the water.

In some embodiments, the schlieren imaging assembly comprises an illumination source, configured to emit any suitable light beam (e.g., visible light), and a schlieren camera, configured to acquire schlieren images of turbulence occurring in the water when injecting the irrigation fluid, through the catheter irrigation holes, into the water.

In other embodiments, the fluid injected through the catheter irrigation holes may comprise water or any other suitable fluid, which is injected at a temperature different (e.g., in at least 10° C.) from that of the water within the container. Note that the refractive index of water (and water-based fluids) decreases with increasing temperature. In the present example, when illuminating the container using a green light having a wavelength of about 550 nm, the refractive index of water having a temperature of 37° C. is about 1.3323546, and the refractive index of water a temperature of about 50° C. is about 1.3303442. The schlieren camera is configured to sense the difference in refractive index that occur across a field of view of the schlieren camera acquiring the schlieren image.

In some embodiments, the processor is configured to visualize and display the irrigation using the schlieren images. Note that when injecting irrigation fluid (such as water or any other at least partially transparent fluid) at a temperature of about 50° C. into the container having water at a temperature of about 37° C., the temperature difference is reduced with the distance from the irrigation holes. Thus, the difference between the refractive indices of the water and irrigation fluid is also reduced with the distance from the irrigation holes. However, the difference between the aforementioned refractive indices is still apparent at a distance of about 3 cm or 5 cm or even further from the irrigation holes, which is larger than a cavity of a typical patient heart undergoing RF ablation.

In some embodiments, based on a plurality of schlieren images, the processor is configured to produce a video display indicative of the temperature gradient between the irrigation holes and a reference point (e.g., resembling an irrigated tissue during RF ablation), so as to estimate the irrigation effectiveness of the tested catheter under predefined conditions, such as pressure and temperature of the injected irrigation fluid.

The disclosed techniques improve the quality and planning of medical procedures involving irrigation by providing a user of an irrigation catheter with characterization and predicted effectiveness of the catheter irrigation. Moreover, the disclosed techniques improve the patient safety in medical procedures, such as in RF ablation, by testing and documenting, for predefined irrigation conditions, the irrigation effectiveness of each catheter before being used during RF ablation or any other procedure that requires in-vitro irrigation.

System Description

FIG. 1 is a schematic pictorial illustration of a system 11 for visualizing catheter irrigation, in accordance with an embodiment of the present invention. In some embodiments, system 11 may be used for characterizing catheters during product development, and/or for testing catheters during production, and/or for planning a medical procedure, such as radiofrequency (RF) ablation of tissue in patient heart.

In some embodiments, system 11 comprises a fluid container 28, a pump 12, a schlieren imaging assembly 42, and a control console 30. Schlieren imaging assembly 42 comprises a schlieren camera 44 described below and an illumination source 43, which is configured to direct light beams having any suitable wavelength or range of wavelengths. In the present example, illumination source 43 is configured to direct a green light beam having a wavelength of about 550 nm, but in other embodiments, illumination source 43 may direct one or more light beams having any other suitable wavelength or range of wavelengths. For example, a visible light having a wavelength between about 400 nm and 750 nm, and an infrared (IR) light (e.g., having a wavelength or range of wavelengths between about 750 nm and 0.8 mm).

In the context of the present disclosure and in the claims, the terms "about" or "approximately" for any numerical values or ranges indicate a suitable dimensional tolerance that allows the part or collection of components to function for its intended purpose as described herein.

In some embodiments, fluid container 28 is typically made from glass or plastic or any other material, which is transparent at least to the light beam directed by illumination source 43. Fluid container 28 is configured to contain a first liquid, which is at least partially transparent to the light beam directed by illumination source 43, and to any other selected wavelength or range of wavelengths. In the present example, the first liquid comprises water 26 having a temperature resembling the temperature of a patient blood (e.g., between about 36° C. and 38° C.).

In some embodiments, fluid container 28 is further configured to receive into water 26, a catheter 22 having one or more irrigation holes 24 for injecting a fluid 33, into the water contained within container 28. In the present example, fluid 33 is at least partially transparent to any of the wavelengths of light described above, and typically resembles irrigation fluid used in RF ablation and/or other types of irrigation fluids used in other sorts of medical procedures. For example, fluid 33 may comprise any suitable type of a saline solution used in irrigation fluids.

In some embodiments, pump 12 is configured to supply fluid 33 between a reservoir 18 and catheter 22, via irrigation tubes 14. Fluid 33 may have any temperature suitable for testing the irrigation of catheter 22, for example, between about 25° C. and 70° C., which must be sufficiently different from the temperature of water 26. In the present example, water 26 and fluid 33 may have a temperature of about 37° C. and 50° C., respectively.

In some embodiments, when illumination source 43 illuminates container 28 using a green light having a wavelength of about 550 nm, the refractive index of water at a temperature of about 37° C. is about 1.3323546. Similarly, the refractive index of water is about 1.3303442 at a temperature of about 50° C.

In some embodiments, schlieren camera 44 of schlieren imaging assembly 42, is configured to acquire schlieren images of turbulence occurring in water 26 when injecting fluid 33, through irrigation holes 24, into water 26. The schlieren images are described in more detail herein. In the present example, schlieren camera 44 comprises an Alpha A7 III camera, produced by Sony Corporation (Tokyo, Japan), or any other suitable type of camera.

In some embodiments, schlieren camera 44 is configured to sense the difference in the aforementioned refractive indices between different locations across the field of view (FOV) of the camera. Schlieren camera 44 is configured to produce, based on the detected intensity of the light beam directed by illumination assembly 43 and transmitted through fluid container 28, a signal indicative of the distribution of refractive index of the mixed fluids (e.g., mixture of water 26 and fluid 33 in close proximity to irrigation holes 24) within the FOV of schlieren camera 44. Note that the distribution of the refractive indices is indicative of the distribution of the temperature across the FOV.

In some embodiments, the temperature difference between water 26 (or any other fluid within container 28) and fluid 33 (e.g., a saline solution, or water or any other suitable fluid injected through irrigation holes 24), is typically larger than about 10° C., but can be any other temperature difference larger than 1° C.

In some embodiments, fluid container 28 may have a scale (not shown), which may be used by processor 55 to calculate a gradient of the temperature as a function of the distance from irrigation hole 24. Additionally or alternatively, processor 55 is configured to estimate the temperature profile or gradient based on the redefined position and magnification of schlieren camera 44.

In some embodiments, control console 30 comprises a processor 55, typically a general-purpose computer, with suitable front end and interface circuits for receiving signals from schlieren camera 44 and for controlling (by sending control signals, via electrical cables 16 to) several components of system 11, such as but not limited to pump 12, schlieren camera 44 and illumination source 43 of schlieren imaging assembly 42.

In some embodiments, processor 55 may be programmed in software to carry out the functions that are used by the system, and the processor stores data for the software in a memory 56 of console 30. The software may be downloaded to console 30 in electronic form, over a network, for example, or it may be provided on non-transitory tangible media, such as optical, magnetic or electronic memory media. Alternatively, some or all of the functions of processor 55 may be carried out by dedicated or programmable digital hardware components.

In some embodiments, control console 30 comprises a display 36 for displaying information and images described below, and input devices 40.

In some embodiments, processor 55 is configured to receive from schlieren camera 44, via electrical cable 16, signals indicative of the one or more schlieren images acquired during the irrigation (in the present example, testing of the irrigation), e.g., when injecting fluid 33 into water 26.

In some embodiments, processor 55 is configured to visualize the irrigation using the schlieren images received from schlieren camera 44. In some embodiments, processor 55 is configured to display, on display 36 of control console 30, an image 66, which is a visualization of the irrigation, based on the signals detected in the FOV of schlieren camera 44. In the present example, image 66 shows imaging of turbulence 60 occurring in water 26 when injecting fluid 33, through irrigation holes 24. Note that catheter 22 is opaque to the light beam directed by illumination source 43, and therefore, appears dark in image 66.

In some embodiments, processor 55 is configured to control schlieren camera 44 to acquire schlieren images in any suitable frequency for producing one or more images 66. For example, processor 55 is configured to control schlieren camera 44 to acquire at least thirty (30) frames of schlieren images per second, so as to produce a video of the irrigation process.

In some embodiments, schlieren imaging assembly 42 may comprise multiple illumination sources 43, each of which configured to direct a light beam having one or more predefined wavelengths, and one or more schlieren cameras 44, configured to acquire the schlieren images. For example, schlieren imaging assembly 42 may comprise (i) a first schlieren camera 44, which is configured to acquire a first schlieren image at a first viewing angle relative to the orientation of catheter 22, and (ii) a second schlieren camera (not shown) which is configured to acquire a second schlieren image at a second viewing angle, different from the first viewing angle.

In some embodiments, at least one of, and typically all of, the schlieren images comprise two-dimensional (2D) schlieren images, acquired from different viewing angles. In an embodiment, processor 55 is configured to visualize the irrigation of catheter 22 by producing, based on the 2D schlieren images acquired from two or more different viewing angles, one or more three-dimensional (3D) schlieren images.

In some embodiments, processor 55 is configured to display a time-series of 3D schlieren images shown in video (e.g., a video clip produced using the thirty frames of schlieren images per second, as described above).

This particular configuration of system 11 is shown by way of example, in order to illustrate certain problems that are addressed by embodiments of the present invention and to demonstrate the application of these embodiments in enhancing the performance of such a visualization and/or testing system. Embodiments of the present invention, however, are by no means limited to this specific sort of example system, and the principles described herein may similarly be applied to other sorts of visualizing and/or testing systems.

Visualizing Catheter Irrigation Using Schlieren Images

Figure 2:
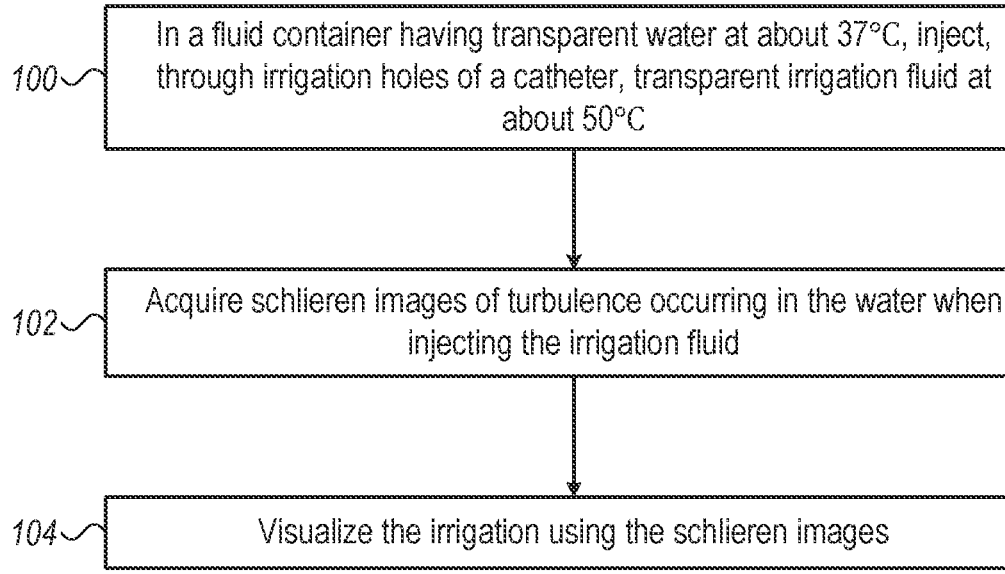
FIG. 2 is a flow chart that schematically illustrates a method for visualizing catheter irrigation, in accordance with an embodiment of the present invention.

FIG. 2 is a flow chart that schematically illustrates a method for visualizing catheter irrigation using schlieren images, in accordance with an embodiment of the present invention.

The method begins at an irrigation fluid injection step 100, with injecting fluid 33, through irrigation holes 24 of catheter 22, into water 26 contained in fluid container 28. In an embodiment, the difference between the temperatures of water 26 and fluid 33 is at least about 10° C. For example, the temperature of water 26 is about 37° C. and the temperature of fluid 33, when injected through irrigation holes 24, is about 50° C.

At a schlieren images acquisition step 102, illumination source 43 directs a light beam towards fluid 33, which is the injected irrigation fluid, and schlieren camera 44, which is typically facing the light beam, acquired one or more schlieren images of turbulence occurring in water 26 when injecting fluid 33. In some embodiments, processor 55 is configured to control illumination source 43 and schlieren camera 44 to continue the illumination and image acquisition for a predefined time interval after concluding the injection of fluid 33, so as to detect the expansion of fluid 33 in water 26, without the injection driving force.

At an irrigation visualization step 104 that concludes the method, processor 55 produces image 66 for visualizing the irrigation using the schlieren images acquired by schlieren camera 44. As described in FIG. 1 above, the irrigation visualization may comprise: (i) one or more schlieren images and/or a video clip for visualizing at least part of the irrigation process, and/or (ii) one or more 3D schlieren images produced based on one or more 2D schlieren images acquired from by two or more cameras from two or more different viewing angles.

Figure 3:
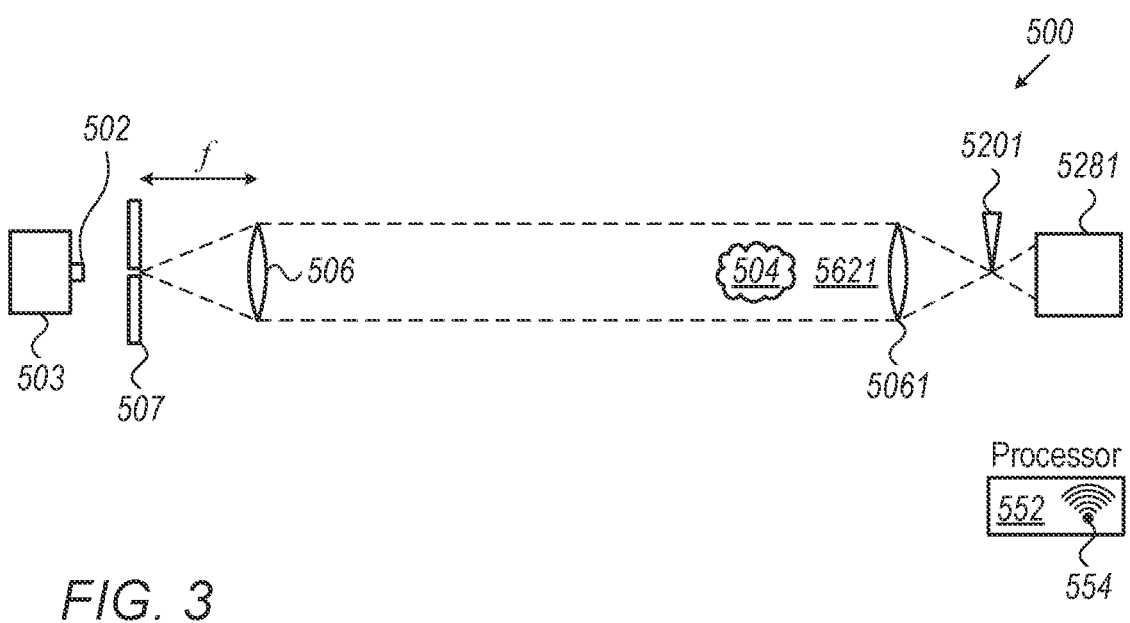
FIG. 3 is a pictorial top view, schematically illustrating an apparatus for visualizing fluid turbulence caused by catheter irrigation, in accordance with another embodiment of the present invention.

FIG. 3 is a pictorial top view, schematically illustrating an apparatus 500 for visualizing fluid turbulence caused by injection of irrigation fluid 33 into water 26, in accordance with another embodiment of the present invention.

In some embodiments, apparatus 500 comprises a bright monochromatic light source, such as a light emitting diode (LED) 502 that is thermally coupled to a heat sink 503. In some embodiments, LED 502 together with a pinhole 507 and a lens 506 (comprising a lens assembly of one or more lenses), which is positioned at a focal length f from pinhole 507, form a source of a plane wave of collimated light, incident through the optical path of apparatus 500.

In some embodiments, the wave is transmitted to incident turbulent media 504, in the present example, fluid turbulence caused by the injection of fluid 33 into water 26 as shown in FIG. 1 above. The wave passing through turbulent media 504 produces a plane wave 5621, which contain information of the turbulence.

In some embodiments, apparatus 500 comprises a lens 5061 comprising an assembly of one or more lenses, which is configured to focus the collimated light of plane wave 5621 onto a knife edge 5201.

In some embodiments, apparatus 500 further comprises a video camera 5281 having suitable optics configured for acquiring the focused beam passing through knife edge 5201, and producing a 2D schlieren images.

In some embodiments, the components of apparatus 500 are controlled a processor 552, using electrical leads (not shown) and/or one or more wireless communication devices (WCDs) 554, depending on system design.

In such embodiments, apparatus 500 is configured to produce a time-series of 2D schlieren images corresponding to respective time instances of the turbulence occurring in water 26 when injecting irrigation fluid 33 through irrigation holes 24.

In other embodiments, apparatus 500 may comprise an additional optical path, which may be produced by splitting the incident collimated beam (used a beam splitter) or using any other suitable technique, and a suitable optical path comprising, inter alia, an additional focusing lens (similar to lens 5061), a knife edge (similar to knife edge 5201) and a video camera (such as video camera 5281).

In some embodiments, processor 552 is configured to produce, based on the two 2D schlieren images, a set of three-dimensional (3D) schlieren images corresponding to respective time instances, and furthermore a 3D video movie of the turbulence caused by the injection of irrigation fluid 33 into water 26.

The configuration of apparatus 500 is simplified for the sake of conceptual clarity and provided by way of example. In other embodiments, processor 55 of system 11 (shown in FIG. 1 above) may be used in addition to or instead of processor 552, and additional components of the optical path may be added.

Although the embodiments described herein mainly address visualization of irrigation fluid, the methods and systems described herein can also be used in other applications, such as in any study and/or visualization and/or measurement of fluidics performance. For example, any dynamic mixture of two or more fluids having one or more different parameters.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system for visualizing catheter irrigation, the system comprising:
   a fluid container, configured to: (i) contain a first fluid, which is at least partially transparent and has a first temperature, and (ii) receive into the first fluid a catheter having one or more irrigation holes;
   a pump, configured to inject, through the one or more irrigation holes, a second fluid, which is at least partially transparent and has a second different temperature;
   a schlieren imaging assembly, configured to acquire schlieren images of turbulence occurring in the first fluid when injecting the second fluid; and
   a processor, which is configured to visualize the irrigation using the schlieren images.

2. The system according to claim 1, wherein the first fluid comprises water and the second fluid comprises water or a saline solution.

3. The system according to claim 1, wherein the first temperature and the second temperature have a difference of at least 1 degree Celsius.

4. The system according to claim 1, wherein the schlieren imaging assembly comprises: (i) one or more illumination sources, wherein at least one of the illumination sources is configured to direct a light beam having one or more predefined wavelengths, and (ii) one or more schlieren cameras, configured to acquire the schlieren images.

5. The system according to claim 4, wherein the schlieren cameras comprise: (i) a first schlieren camera, configured to acquire a first schlieren image at a first viewing angle, and (ii) a second schlieren camera, configured to acquire a second schlieren image at a second different viewing angle.

6. The system according to claim 5, wherein the first and second schlieren images comprise two-dimensional (2D) schlieren images, and wherein the processor is configured to visualize the irrigation by producing, based on the 2D schlieren images, one or more three-dimensional (3D) schlieren images.

7. The system according to claim 6, wherein the processor is configured to display a time-series of the 3D schlieren images in video.

8. The system according to claim 1, wherein the fluid container is at least partially transparent to the light beam and has a scale, and wherein the processor is configured to calculate a gradient of the temperature, between the first and second temperatures, using the scale.

9. A method for visualizing catheter irrigation, the method comprising:

in a fluid container having a first fluid, which is at least partially transparent and has a first temperature, injecting, through one or more irrigation holes of a catheter, a second fluid, which is at least partially transparent and has a second different temperature;

acquiring schlieren images of turbulence occurring in the first fluid when injecting the second fluid; and visualizing the irrigation using the schlieren images.

10. The method according to claim 9, wherein the first fluid comprises water and the second fluid comprises water or a saline solution.

11. The method according to claim 9, wherein the first temperature and the second temperature have a difference of at least 1 degree Celsius.

12. The method according to claim 9, wherein acquiring schlieren images comprises directing a light beam having one or more predefined wavelengths, and acquiring the schlieren images of the turbulence occurring in the first fluid when injecting the second fluid.

13. The method according to claim 12, wherein acquiring schlieren images comprises acquiring a first schlieren image at a first viewing angle and acquiring a second schlieren image at a second different viewing angle.

14. The method according to claim 13, wherein the first and second schlieren images comprise two-dimensional (2D) schlieren images, and wherein visualizing the irrigation comprises producing, based on the 2D schlieren images, one or more three-dimensional (3D) schlieren images.

15. The method according to claim 13, wherein visualizing the irrigation comprises displaying a time-series of the 3D schlieren images in video.

16. The method according to claim 9, wherein the fluid container is at least partially transparent to a light beam used for acquiring the schlieren images and has a scale, and comprising calculating a gradient of the temperature, between the first and second temperatures, using the scale.

* * * * *